(12) United States Patent
Ayyappanpillai et al.

(10) Patent No.: US 9,791,451 B2
(45) Date of Patent: Oct. 17, 2017

(54) SQUARAINE BASED FLUORESCENT PROBE AND A PROCESS FOR THE PREPARATION THEREOF

(71) Applicant: Council of Scientific & Industrial Research, New Delhi (IN)

(72) Inventors: Ajayaghosh Ayyappanpillai, Trivandrum (IN); Anees Puravan, Trivandrum (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/914,717

(22) PCT Filed: Dec. 9, 2013

(86) PCT No.: PCT/IN2013/000757
§ 371 (c)(1),
(2) Date: Feb. 26, 2016

(87) PCT Pub. No.: WO2015/029050
PCT Pub. Date: Mar. 5, 2015

(65) Prior Publication Data
US 2016/0209419 A1 Jul. 21, 2016

(30) Foreign Application Priority Data
Aug. 30, 2013 (IN) .......................... 2564/DEL/2013

(51) Int. Cl.
| | |
|---|---|
| C09B 57/00 | (2006.01) |
| G01N 33/68 | (2006.01) |
| G01N 33/84 | (2006.01) |
| G01N 21/64 | (2006.01) |
| G01N 33/58 | (2006.01) |

(52) U.S. Cl.
CPC ......... *G01N 33/582* (2013.01); *C09B 57/007* (2013.01); *G01N 21/6428* (2013.01); *G01N 33/68* (2013.01); *G01N 33/84* (2013.01); *G01N 2021/6439* (2013.01); *G01N 2333/765* (2013.01)

(58) Field of Classification Search
CPC ...... C09B 57/00; G01N 33/582; G01N 33/68; G01N 33/84
See application file for complete search history.

(56) References Cited

PUBLICATIONS

Hirose et al., Caplus an 1990:506345.*
Anees et al., Caplus an 2014:1510339.*
Sreejith, S. et al., "A Near-Infrared Squaraine Dye as a Latent Ratiometric Fluorophore for the Detection of Aminothiol Content in Blood Plasma", *Angewandte Chemie* 120(41): 8001-8005 (2008).
Ros-Lis, J. V. et al., "Squaraines as Fluoro-Chromogenic Probes for Thiol-Containing Compounds and Their Application to the Detection of Biorelevant Thiols", *Journ. Am. Chem. Soc.* 123(13): 4064-4065 (2004).
Zhou, K. et al., "Multicolored pH-Tunable and Activatable Fluorescence Nanoplatform Responsive to Physiologic pH Stimuli", *Journ. Am. Chem. Soc.* 134(18):7803-7811 (2012).
Hyo Sung Jung et al., "Coumarin-Based Thiol Chemosensor: Synthesis, Turn-On Mechanism, and Its Biological Application", *Organic Letters* 13(6):1498-1501 (2011).
International Preliminary Report on Patentability, dated Mar. 10, 2016, PCT/IN2013/000757.
International Search Report, dated Jul. 21, 2014, PCT/IN2013/000757.

* cited by examiner

*Primary Examiner* — Sun Jae Yoo
(74) *Attorney, Agent, or Firm* — Seyfarth Shaw LLP

(57) ABSTRACT

The present invention describes the use of a fluorescent NIR dye for various applications by simply changing the solvent conditions. Molecule of formula 1 in the monomeric state (30% ACN/25 mM phosphate buffer) can be used for the sensitive detection of thiols and monitoring minor fluctuations in the thiol concentration inside live cells. Molecule 1 in the self-assembled state (25 mM phosphate buffer) can be used for labeling of serum albumin protein either covalently or noncovalently at specific pH. The probe 1 specifically bind with the serum albumin proteins noncovalently at lower pH gives a "turn-on" NIR emission whereas it binds covalently at higher pH gives a "turn-on" green fluorescence. Since the probe detects serum albumin proteins selectively in presence of other thiol containing small molecules, the probe can be used as an excellent sensor for serum albumin proteins. The dye-protein complex of various ratios can be used as sensors to detect the pH variations in a broad window from 4.6-11.6 with high sensitivity. Due to the high biocompatibility and water solubility the dye protein complex is useful for ratiometric detection of minor pH variations inside cellular environment.

Formula 1

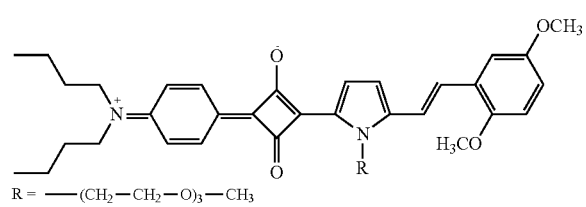

R = —(CH$_2$—CH$_2$—O)$_3$—CH$_3$

13 Claims, 12 Drawing Sheets

DAPI Images

Alexa Images

Bright field Images

SQUARAINE BASED FLUORESCENT PROBE AND A PROCESS FOR THE PREPARATION THEREOF

FIELD OF INVENTION

Figure 1:
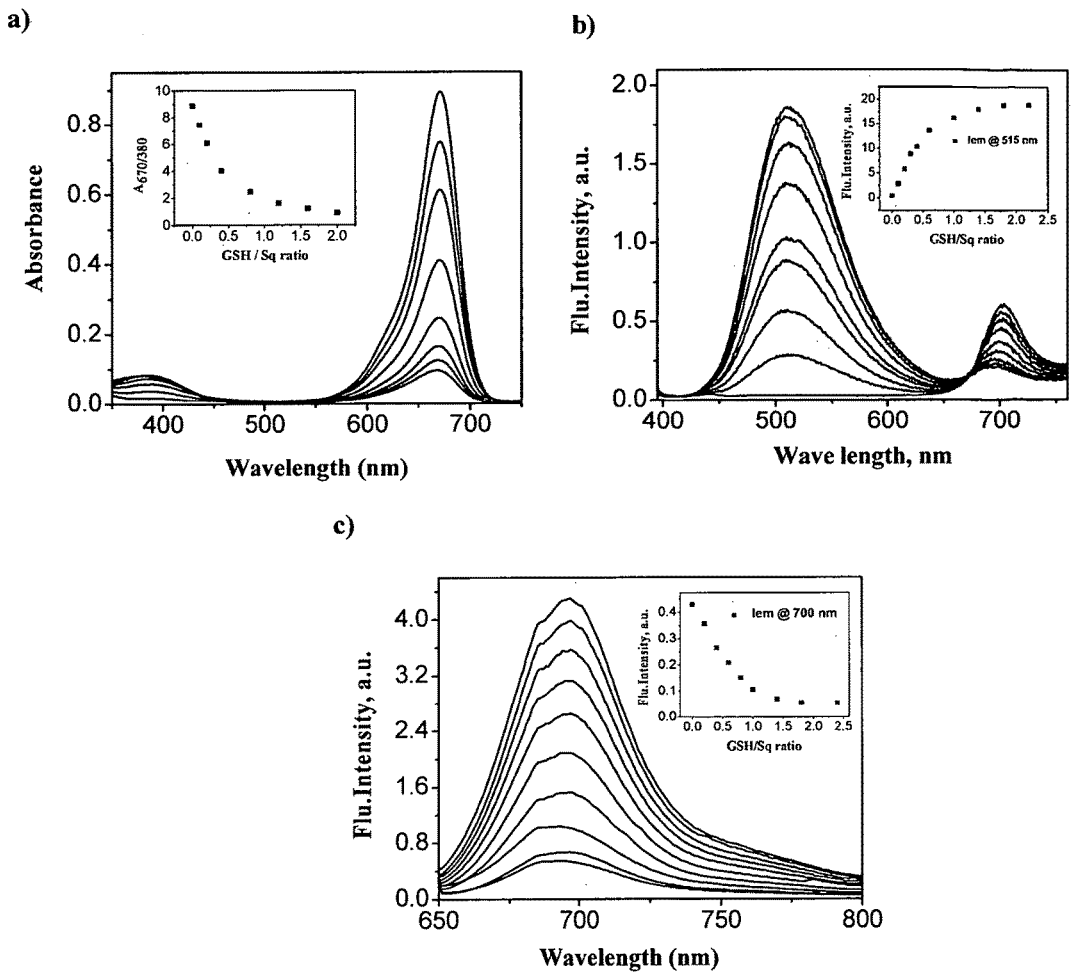

The present invention relates to a squaraine based fluorescent probe of formula 1 for thiol imaging, selective labeling and sensing of serum albumin. The present invention also relates to detection of thiols with very high sensitivity and monitoring minor fluctuations in the thiol concentration inside live cells between millimolar to micromolar range. More particularly the present invention also relates to use a 1:6 dye—protein complex to monitor minor pH variations in biological medium.

Formula 1

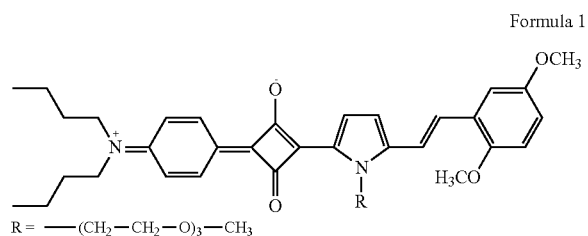

R = —(CH$_2$—CH$_2$—O)$_3$—CH$_3$

BACKGROUND OF THE INVENTION & DESCRIPTION OF PRIOR ART

Biological thiols play a major role in regulating various biological events such as redox-methyl transfer and CoA-related reactions. The concentration levels of intracellular thiols change dramatically in response to oxidative stress, which has been associated with a number of diseases, including cancer, AIDS, Alzheimer's and cardiovascular disease. Therefore, the rapid, highly sensitive, and selective determination of intracellular thiols is of great importance for investigating its role in cellular functions and disease detection and diagnosis. Among the various analytical techniques employed today, optical detection has proven to be the most convenient methods of all and fluorescence is an important optical detection method due to its high sensitivity, low detection limit and have an advantage of intracellular detection.

Fluorescence based thiol sensors owing to the nucleophilicity of thiols undergo Michael addition, cyclisation with aldehyde, cleavage of sulphonamide, sulfonate ester and disulphide. Squaraine dyes have been extensively investigated as chemosensors and chemodosimeters.

Protein labelling is an important technique that enables the direct visualization of many biological events such as protein functions, protein dynamics, protein—protein interactions and for the detection of various biologically relevant analytes. Labelling strategies with small organic fluorophore have attracted much attention. Depending on the nature of interaction between the receptor protein and the ligand, the labelling can be either high affinity noncovalent or site specific covalent labelling. Herein we report a novel fluorescent molecule that switches the mode of interaction between covalent and noncovalent labelling giving two different spectral responses by changing the pH of the solution and detect the serum albumin protein selectively among other thiol containing competing molecules.

Reference may be made to a symmetrical squaraine based fluorescent probe that detect thiols at physiological pH window with high sensitivity reported by R. M. Manez et al. *J. Am. Chem. Soc.* 2004, 126, 4064. The main drawback is the detection of thiol is based on fluorescence quenching and hence it is not applicable for the detection of intracellular thiol imaging.

Another reference may be made to use a symmetrical squaraine dye that detects thiols ratiometrically reported by A. Ajayaghosh et al. *Angew. Chem. Int. Ed.* 2008, 120, 8001. The main drawback is that the reactivity of the probe is very poor and the detection of thiol occurs at basic pH, 9.6 which we cannot use for the detection of thiol content in cells due to the lack of biocompatibility.

References may be made to fluorescent molecule that detects thiols inside cells which were pre-treated with a thiol deactivating molecule, NEM of concentration 0.2-1 mM reported by S Kim et al. *Org Lett.* 2011, 13, 6. S. Kim et al. *Chem. Commun.*, 2011, 47, 5142. The main drawback is the detection of thiols inside the cells is limited to only in milli molar range.

However, as evident from the above references a fluorescent probe that could image thiol fluctuations inside cells which were pre-treated with NEM of concentrations from milli molar to micro molar range is still unknown.

References may be made to a protein labeling method, termed as ligand-directed tosyl (LDT) chemistry, which can site-specifically introduce a synthetic probe to a protein with the concomitant release of the affinity ligand. The molecule initially forms a complex with protein and then under goes covalent labeling as reported by I. Hamachi. *Nat. Chem. Biol.* 2009, 5, 341. The major drawback is that the spectroscopic response remains the same for both modes of interactions and the initial complex formed is less stable and immediately gives rise to a reaction that allows only covalent labeling, and hence called as affinity based irreversible covalent labeling.

As evident from the above reference, the fluorescent probe in the present invention specifically switches the mode of interaction with proteins between a noncovalent and covalent labeling, which can be controlled with an external stimulus resulting in distinct signal response is a new and novel approach.

Reference may be made to fluorescent pH nanosensor by incorporating two different fluorophores to carbon nanodots. By changing the ratio of these fluorophores functionalised on the surface of carbon nanodots the region of sensitivity in the pH scale can be tuned as reported by H. Ma et al. *Angew. Chem. Int. Ed.* 2012, 51, 1. The drawback of this work is, tuning based on ratio of fluorophores functionalised over carbon nanodots is possible through fresh synthesis of carbon nanodots with fluorophores in different ratios.

Another reference may be made to use fluorescent dyes with polymers that form nanoparticles. Different dyes shows sensitivity in different regions of the pH scale as reported by J. Gao et al. *J. Am. Chem. Soc.* 2012, 134, 7803. The main drawback of this work is that for different regions of sensitivity, polymers with different dyes have to be synthesised separately.

Since the labeling process is reversible with respect to the variation of pH of the solution, we employed the dye-protein complex for monitoring pH variations inside the cells. Intracellular pH plays an important role in regulating various cellular events including cell growth, receptor mediated signal transduction, enzymatic activity, calcium regulation and cell adhesion. Under normal physiological conditions the pH is maintained within a range of 7.35-7.45. Small deviation out of this range can cause cardiopulmonary and neurologic problems (e.g., Alzheimer's disease) and more extreme variations can be fatal. So detection of pH changes inside the cells is of great importance. Small molecular fluorescent probes as well as fluorescent proteins have been widely used for intracellular pH detection. Herein we use the dye protein complex in a particular ratio to monitor minor pH fluctuations inside the cells As evident from the above references, fluorescence based pH sensors either detect the pH changes within a narrow pH window with high sensitivity or detect pH in a broad range with less sensitivity. However a simple probe that can be used to detect pH variations in a broad region with high sensitivity is still not known. Herein we report the dye-protein complexes of various ratios that was prepared just by mixing in different ratios and can be used to detect pH from 4.6-11.6 with high sensitivity.

Squaraine dyes have been used as a colorimetric and fluorescent probe for the detection of thiols. The first report came from R. M. Manez et al. *J. Am. Chem. Soc.* 2004, 126, 4064. In this work the authors have used a symmetrical squaraine dye of aniline derivative for the detection of thiol at physiological (6.5-7.5) pH window with high sensitivity. Since the detection of thiol is basically based on fluorescence quenching, this probe shall not be useful for cell imaging. Later we have reported a symmetrical squaraine dye with two chromophores on both side of the ring which can be activated upon interaction of the thiols (Ajayaghosh et al. *Angew. Chem. Int. Ed* 2008, 120, 8001). Due to the poor reactivity and detection of thiols occur at basic pH window (9.6), the dye was not biocompatible and not useful for cell imaging purposes.

In order to obviate the drawbacks associated with the known squarine dyes there is a need to provide the squarine based fluorescent probes. Accordingly, we have synthesized an unsymmetrical squaraine dye that detects thiols by "turn-on" fluorescence with high sensitivity at physiological (7.2-7.8) pH. This high reactivity at physiological pH window and fluorescence "turn-on" response toward thiols helps the inventors to use this probe for the detection of thiol fluctuations inside the biological cells from milli molar to micro molar ranges.

OBJECTS OF THE INVENTION

The main object of the present invention is to provide a multipurpose squaraine based fluorescent probe.

Another object of the present invention is to provide squaraine based fluorescent probe for selective labeling of serum albumin protein Still another object of the present invention is to provide dye-protein complexes for the minute pH monitoring.

Still another object of the present invention is to develop an NIR dye (a dye that absorb and emit in the near infrared region of the electromagnetic spectra) for the selective labeling of serum albumin protein either covalently or non-covalently from other thiol and non thiol containing proteins and small molecules.

Yet another object of the present invention is to use the NIR dye for the detection of minor fluctuation in the thiol concentration inside the cells.

Yet another object of the present invention is to ascertain that dye in the self-assembled state is non fluorescent, becomes strongly fluorescent when it binds to its target which helps in visualizing the process of labeling reaction immediately at the point of labeling in the presence of unreacted probe.

Still another object of the present invention is to provide self-assembled molecule detects serum albumin protein selectively among other thiol containing small molecules and proteins.

Yet another object of the present invention is to use the of dye-protein complexes for the sensitive detection of pH variations in different regions of the pH scale.

Still another object of the present invention is to use the dye-protein complex for the ratiometric sensitive detection of pH variations in biological medium.

SUMMARY OF THE INVENTION

Accordingly, the present invention provides a novel unsymmetrical Squaraine dye of formula 1 and its complex thereof.

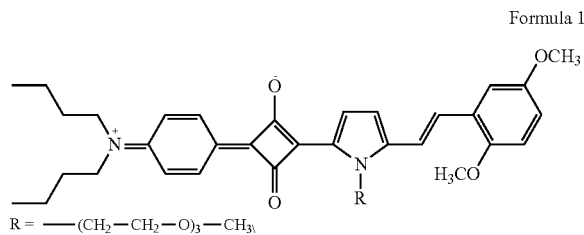

Formula 1

$R = \text{---}(CH_2\text{---}CH_2\text{---}O)_3\text{---}CH_3$

In an embodiment of the invention wherein the compound is useful for the detection of milli molar to micro molar fluctuation in the thiol concentrations inside live cells.

The present invention also provides a process for preparation of compound of formula 1 wherein the steps comprises of
a. reacting N,N-dibutyl aniline in the range of 3 to 0.35 mmol with styrylpyrrole derivative in the range of 3 to 0.35 mmol in isopropanol (40 to 45 ml) along with addition of 1 to 1.2 ml of TBOF,
b. refluxing the mixture at a temperature in the range of 80 to 90° C. for a time period in the range of 10 to 12 hours,
c. cooling the reaction mixture and removing isopropanol by distillation,
d. filtering the crude mixture so obtained and redissolving it in chloroform and further purifying it by column chromatography over silica gel using 2% MeOH/CHCl$_3$ to obtain unsymmetrical Squaraine dye of formula.

The process for the preparation of protein complex wherein the process steps comprises of:
a. preparing a stock solution of squarine dye of formula 1 in acetonitrile of a concentration ranging between $1.2 \times 10^{-3}$ M to $2.4 \times 10^{-3}$ M,
b. preparing a stock solution of BSA or HSA protein in phosphate buffer at a concentration ranging between $2.4 \times 10^{-3}$ M to $2.4 \times 10^{-3}$ M,
c. adding BSA or HSA protein solution as prepared in step (b) to the solution of squarine dye of step (a) in different ratios (1:12 ($1 \times 10^{-6}$ M:$12 \times 10^{-6}$ M), 1:6 ($1 \times 10^{-6}$ M:$6 \times 10^{-6}$ M), 1:1 ($1 \times 10^{-6}$ M:$1 \times 10^{-6}$ M), 1:1/6 ($1 \times 10^{-6}$ M:$0.167 \times 10^{-6}$ M), 1:1/12 ($1 \times 10^{-6}$ M:$0.083 \times 10^{-6}$ M)) at pH solutions ranging between (4.2-11.6) to obtain various Sq-protein complex ($1 \times 10^{-6}$ M to $2 \times 10^{-6}$ M), recording emission spectra after keeping the solution for a time period in the range of 1 hour to 2 hour.

In an embodiment of the invention wherein the squaraine dye of formula 1 in the self-assembled state is useful for the selective noncovalent labeling of serum albumin proteins wherein the pH ranges from 4.2 to 6.0.

In another embodiment of the invention wherein the squaraine dye of formula 1 in the self-assembled state is useful for the selective covalent labeling of serum albumin proteins wherein the pH ranges from 7.2 to 8.8.

In yet another embodiment of the invention wherein the squaraine dye of formula 1 in micro molar concentration undergoes spherical assemblies of size 100-200 nm in water.

In still another embodiment of the invention wherein the squaraine dye of formula 1 in the self-assembled state selectively detects serum albumin proteins among other thiol containing and non-thiol containing proteins.

In one more embodiment of the invention wherein the squaraine dye of formula 1 in the self-assembled state selectively detects serum albumin proteins among other proteins and small molecules at lower pH of (4.2 to 6.0) showing (650-750) NIR emission.

In a further embodiment of the invention wherein the squaraine dye of formula 1 in the self assembled state selectively detects serum albumin proteins among other proteins and small molecules at higher pH of (7.2 to 8.8) showing green fluorescence (450-600 nm).

A nanoprobe of a compound as disclosed in the present invention wherein a combination of the squaraine dye of formula 1 with BSA protein in different ratios (1:12 ($1\times10^{-6}$ M:$12\times10^{-6}$ M), 1:6 ($1\times10^{-6}$ M:$6\times10^{-6}$ M), 1:1 ($1\times10^{-6}$ M:$1\times10^{-6}$ M), 1:1/6 ($1\times10^{-6}$ M:$0.167\times10^{-6}$ M), 1:1/12 ($1\times10^{-6}$ M:$0.083\times10^{-6}$ M)) can be used to monitor minor pH variations in different regions of the pH scale (4.6 to 11.6).

A nanoprobe of the compound as disclosed in the present invention wherein a combination of the squaraine dye of formula 1 with protein (BSA or HSA) with ratio 1:6 can be used for the imaging of biological cell samples for monitoring (6.5-7.5) pH variations.

In one more embodiment of the invention wherein the method for thiol imaging in cells comprises of following steps:
  a. incubating the Hep-G2 cells with NEM of concentration in the range of $3\times10^{-3}$ M to $3\times10^{-6}$ M and for a time period of 15 minutes to 20 minutes,
  b. adding squaraine dye of formula 1 ($1.2\times10^{-3}$ M) prepared in acetonitrile to cells and keeping it for 10 minutes,
  c. cells were washed to remove the squaraine dyes outside the cells by centrifugation for 2 times, imaging the cells so obtained using confocal fluorescence microscope using alexa (640 nm exc) and DAPI (380 nm exc) as filters.

In still another embodiment of the invention wherein a method for the imaging of pH changes in cells comprises of following steps:
  a. pre-incubating Hep-G2 cells with phosphate buffer at a pH in the rabge of 6.5 to 7.5 and keeping it for 10 minutes,
  b. adding a combination of 1:6 Sq-BSA ($1\times10^{-6}$M), to each cells and keeping it for 10 minutes,
  c. centrifuging the cells so obtained and diluting it for 2 times,
  d. imaging was done using confocal fluorescence microscope using alexa (640 nm exc) and DAPI (380 nm exc) as filters.

BRIEF DESCRIPTION OF THE ACCOMPANYING DRAWINGS

Formula 1 Shows the molecular structure of the unsymmetrical squaraine dye 1.

FIG. 1: Shows (a) UV/Vis absorption and (b) & (c) emission spectral changes of Sq (2 μM, 30% ACN/25 mM phosphate buffer) upon addition of GSH at a pH 8.0, $\lambda_{exc}$ @ 380 nm and 640 nm respectively.

Figure 2:
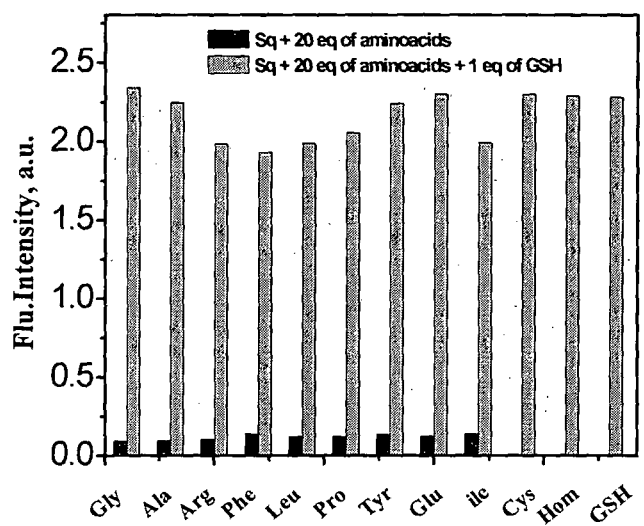

FIG. 2: Fluorescence responses at 510 nm ($\lambda_{exc}$ @ 380 nm) of Sq (2 μM, 30% ACN/25 mM phosphate buffer, pH 8.0) to different amino acids at a pH 8.0. Black bars represent fluorescence intensity upon addition of 20 equivalence different amino acids and gray bar represent the subsequent addition of 1 equivalent of GSH to the mixture.

Figure 3:
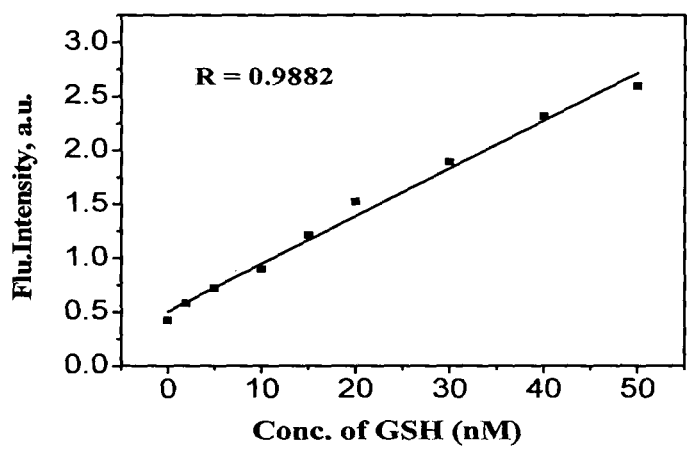
Figure 4A:
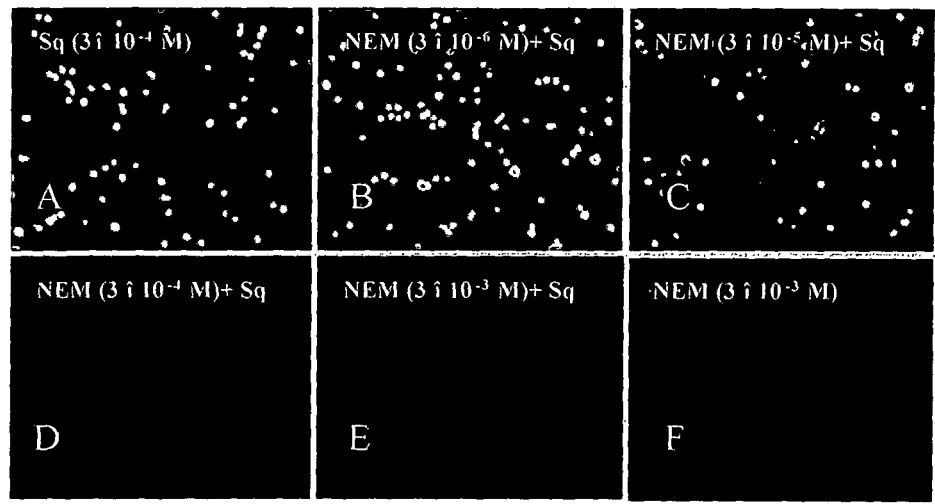
Figure 4B:
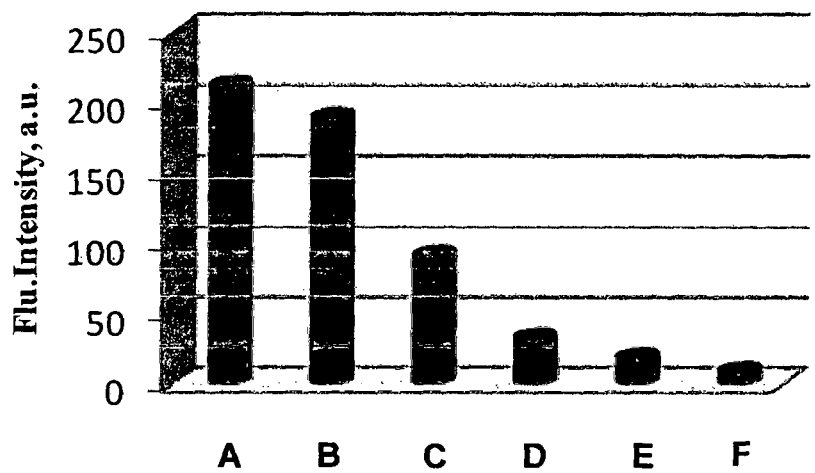

FIG. 3 Plot of fluorescence intensity of Sq at 510 nm ($\lambda_{exc}$ @ 380 nm) as a function of GSH concentration in the 2-100 Nm FIG. 4: (a) Confocal fluorescence microscopic images of HepG2 cells pre-treated with NEM (N-ethyl maleimide, thiol deactivating molecule) of various concentrations followed by the incubation of Sq dye. Images of the cells were obtained using excitation at 380 nm and a long-path (>410 nm) emission filter (b) Fluorescence intensity at 510 nm ($\lambda_{exc}$ @ 380 nm) obtained from Hep-G2 cells (FIG. 4a) plotted against NEM of various concentrations.

Figure 5:
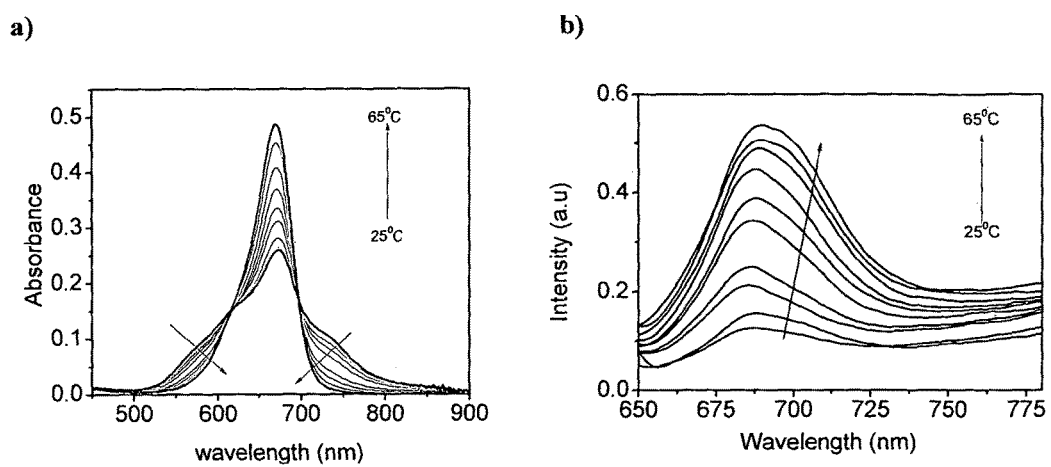

FIG. 5: Shows temperature dependent (a) absorption and (b) emission spectra of 1 ($6\times10^{-6}$M) in 15% acetonitrile/25 mM phosphate buffer solution.

Figure 6:
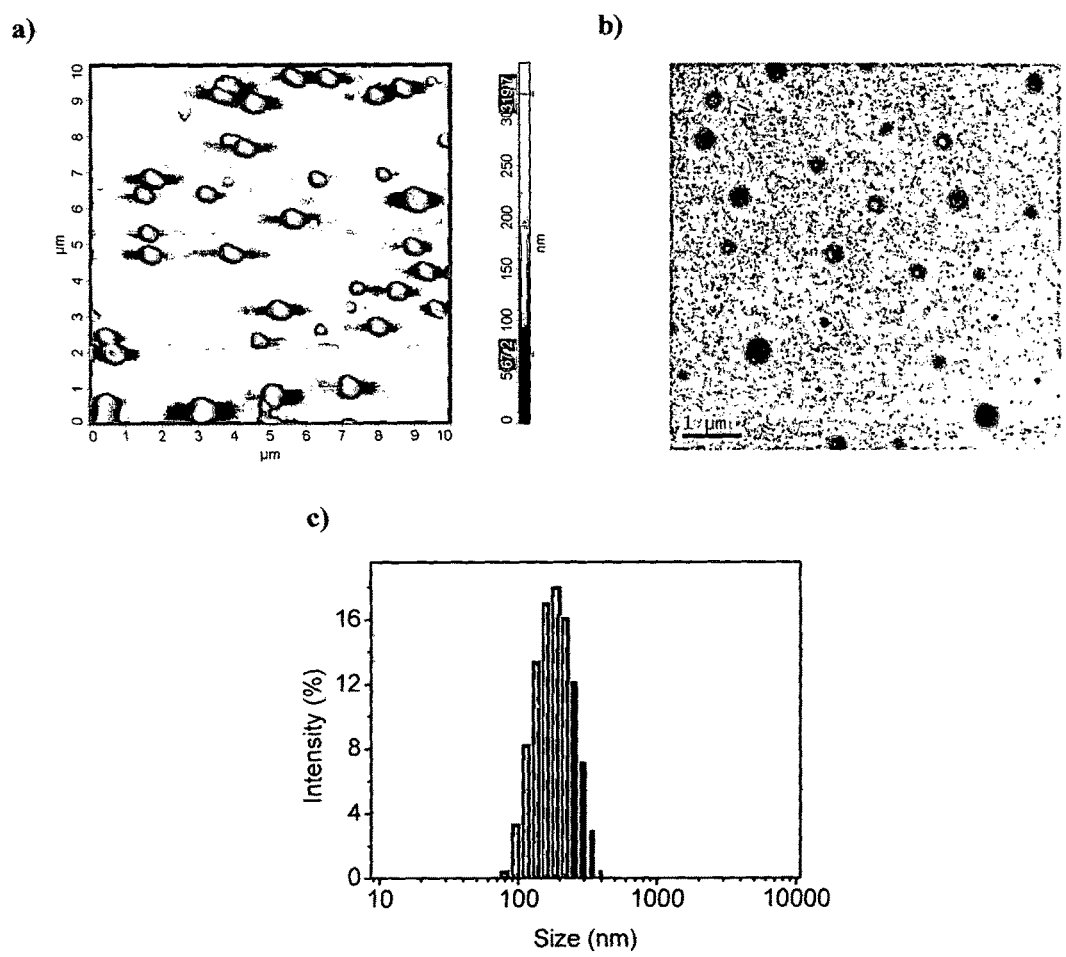

FIG. 6: (a) AFM (b) TEM and (c) DLS analysis of the self-assembled probe 1 ($6\times10^{-6}$M) in 25 mM phosphate buffer (pH 4.2).

Figure 7:
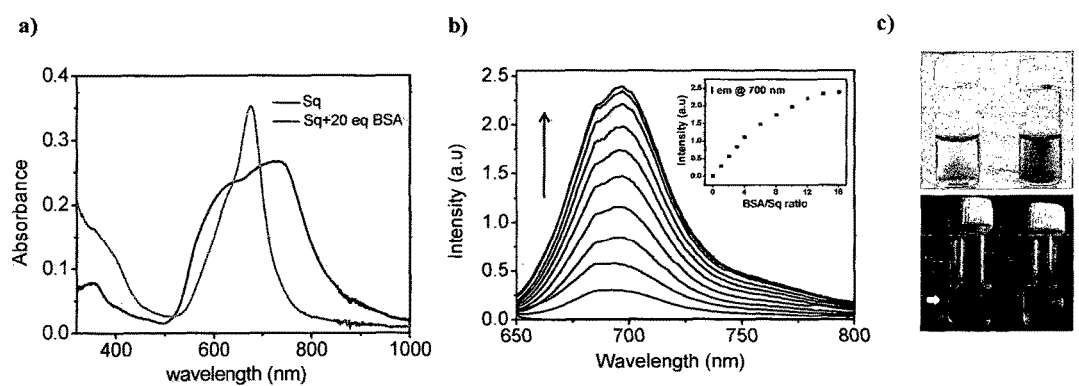

FIG. 7: Shows a) absorption and b) emission spectra of 1 ($6\times10^{-6}$M) with increase in addition of BSA protein in 25 mM phosphate buffer having pH 4.2. Fig (c) is the photographs of Sq before and after addition of BSA protein at pH 4.2. The top figure shows the visual color change and the bottom figure shows the corresponding fluorescence color change.

Figure 8:
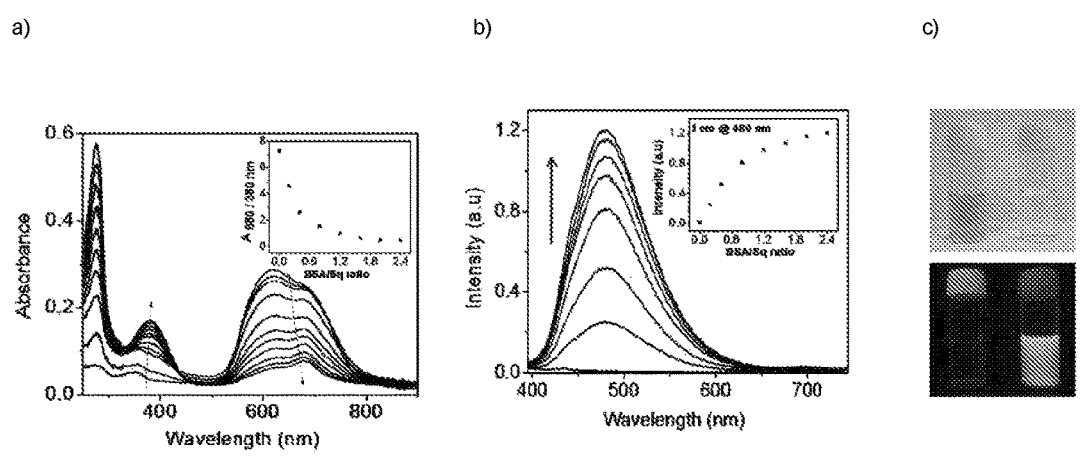

FIG. 8: Shows a) absorption and b) emission spectra of 1 ($6\times10^{-6}$M) with increase in addition of BSA protein in 25 mM phosphate buffer having pH 8.2. Fig (c) is the photographs of Sq before and after addition of BSA protein at pH 8.2. The top figure shows the visual color change and the bottom figure shows the corresponding fluorescence color change.

Figure 9:
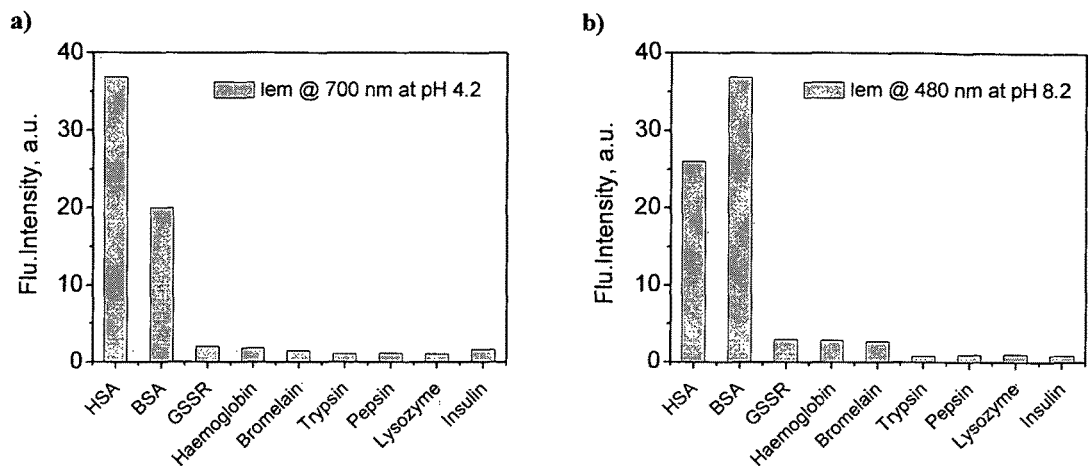

FIG. 9: Selectivity of 1 towards BSA and HSA protein from other thiol and nonthiol containing proteins. (a) Plot of fluorescence intensity of 1 (6 μM) monitored at 700 nm ($\lambda_{ex}$@ 640 nm) at a pH 4.2 with 10 equivalence of different proteins and (b) Plot of fluorescence intensity of 1 (6 μM) monitored at 480 nm ($\lambda_{ex}$@ 380 nm) at a pH 8.2 with 1 equivalence of BSA and HSA and 10 equivalence of other proteins.

Figure 10:
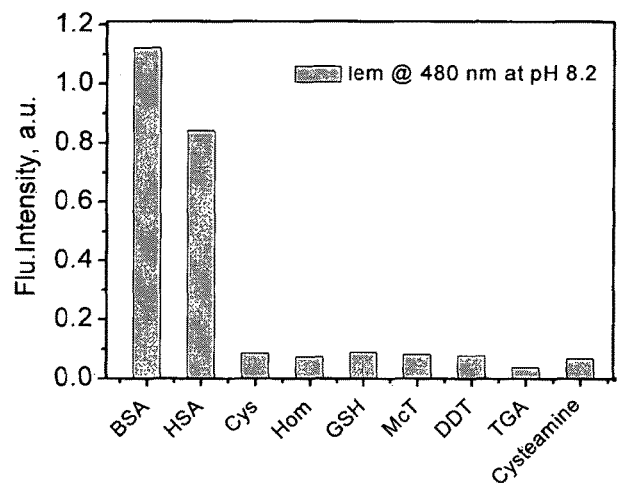

FIG. 10 Selectivity of 1 towards BSA and HSA protein from other small thiol containing molecules. Plot of fluorescence intensity of 1 (6 μM) monitored at 480 nm ($\lambda_{ex}$@ 380 nm) at a pH 8.2 with 1 equivalence of BSA and HSA and 10 equivalence of other small thiol containing molecules.

Figure 11:
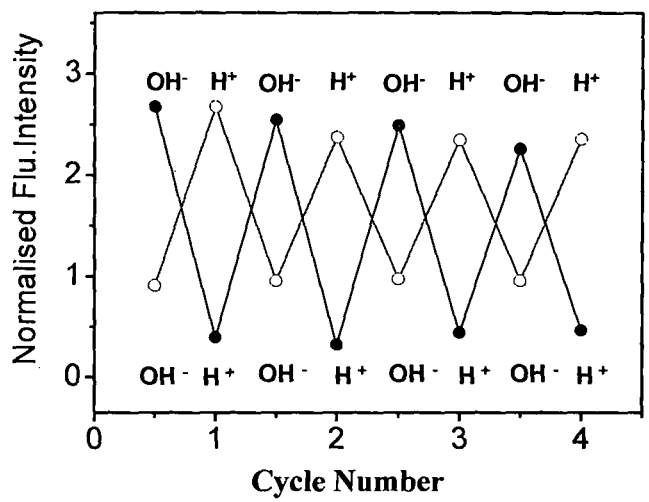

FIG. 11 Fluorescence responses of 1:6 Sq-BSA complex to acid/base cycles. Fluorescence intensity at 700 nm ($\lambda_{exc}$ @ 640 nm) and 480 nm ($\lambda_{exc}$ @ 380 nm) were monitored.

Figure 12:
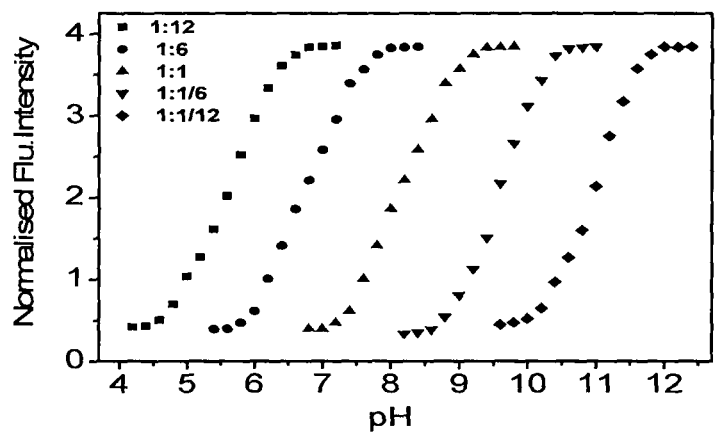

FIG. 12 Normalized emission spectra of Sq (1 μM) at 480 nm ($\lambda_{ex}$ 380 nm) for various composition of Sq-BSA complex against pH of the solution.

Figure 13:
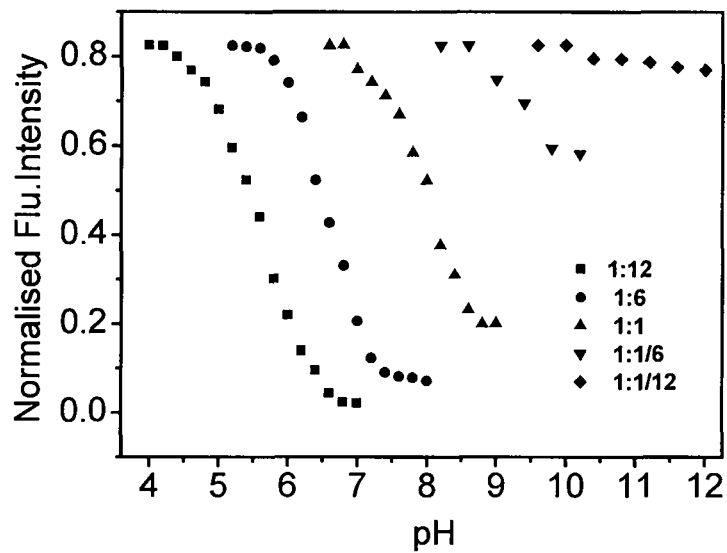

FIG. 13 Normalized emission spectra of Sq (1 μM) at 700 nm ($\lambda_{ex}$ 640 nm) for various composition of Sq-BSA complex against pH of the solution.

Figure 14:
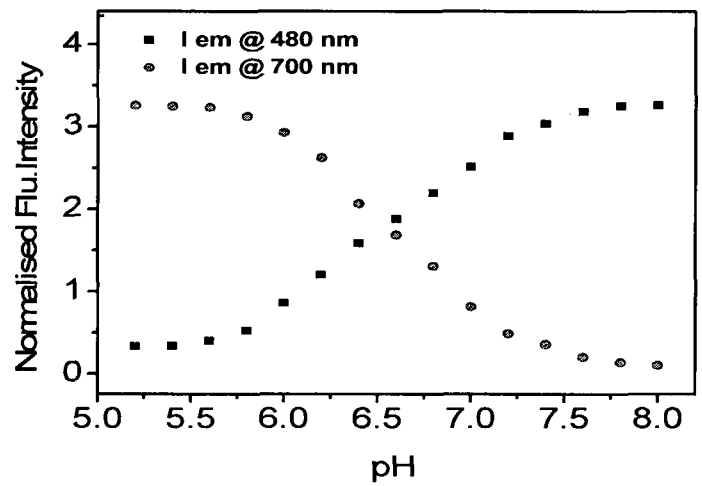

FIG. 14: Ratiometric fluorescence change for 1:6 Sq-BSA (1 μM) complex observed in the physiological pH window (6.4-7.6). Plot of fluorescence intensity of 1:6 Sq-BSA complex (1 μM) (●) monitored at 700 nm ($\lambda_{ex}$@ 640 nm)

and (■) monitored at 480 nm ($\lambda_{ex}$@ 380 nm) with respect to increase in pH of the solution.

Figure 15:
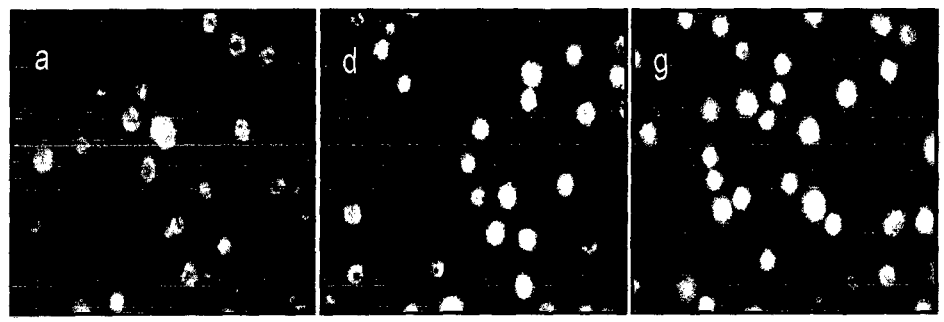
Figure 15:
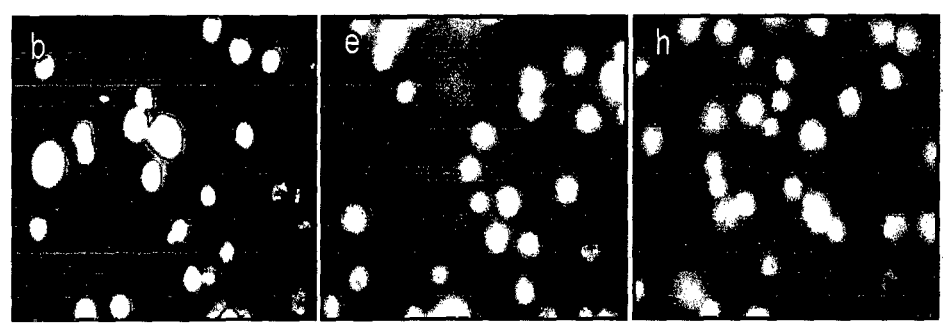
Figure 15:
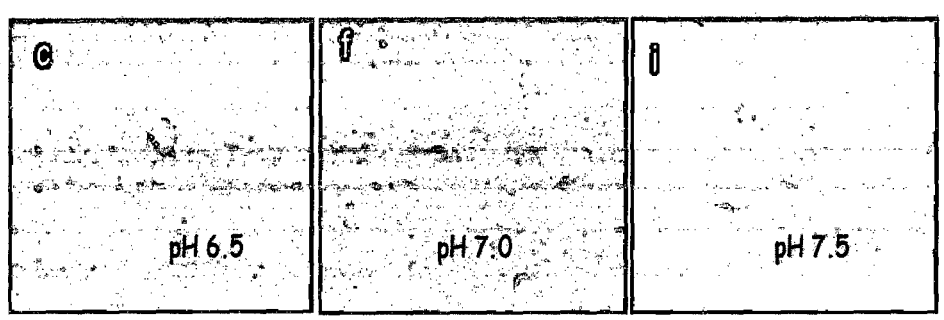

FIG. 15: Shows confocal fluorescence microscopic images of Hep-G2 cells incubated with 1:6 Sq-BSA complex at pH 6.5 (a-c) 7.0 (d-f) and 7.5 (g-i).

Figure 16:
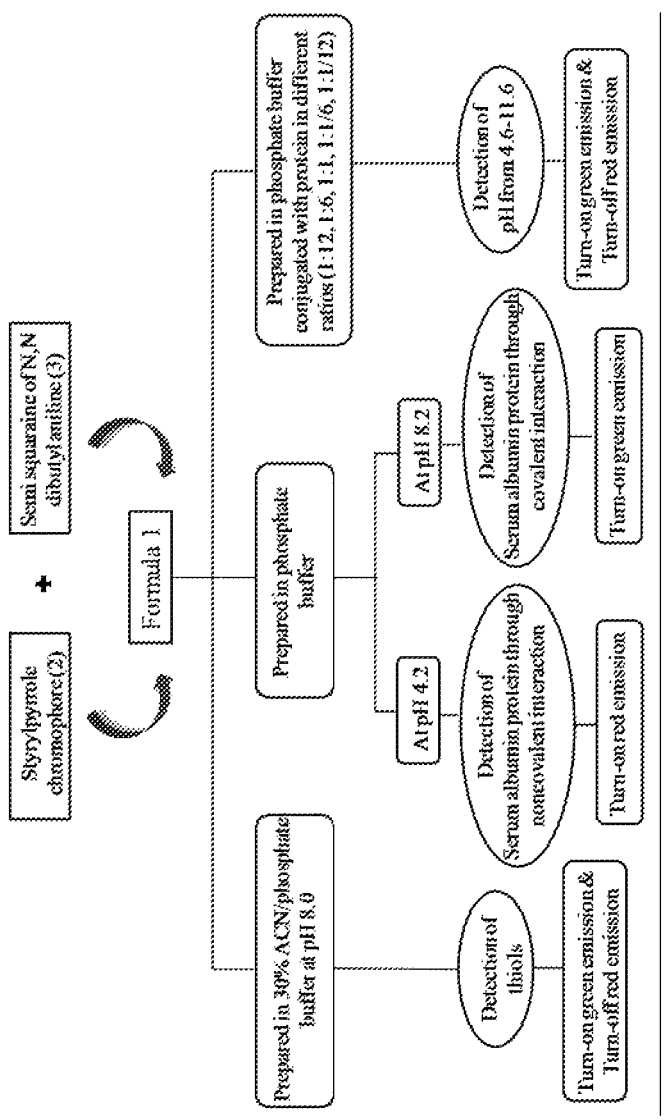

FIG. 16: shows a flowchart for using the unsymmetrical Squaraine dye of formula 1.

Table 2 Fluorescence intensity is obtained from cells using software Bio-Rad Image Data Explorer.

LIST OF ABBREVIATIONS USED & DEFINITION

Sq Squaraine dye
ACN Acetonitrile
NEM N-ethyl maleimide
GSH Glutathione
Cys Cysteine
Hcys Homocysteine
Hep-G2 Human hepatoma cell
AFM Atomic force microscopy
TEM Transition electron microscopy
DLS Dynamic light scattering
BSA Bovine serum albumin
HSA Human serum albumin
TBOF Tributyl orthoformate
MeOH Methanol
$CHCl_3$ Chloroform
NIR Near infrared
Molecular probe A molecular probe is a molecule or molecular material that uses to detect, sense, or quantify analytes of interest such as ions molecules, macromolecules, molecular aggregates, proteins or organisms.
Nanoprobe The term nanoprobe is used to describe a probe at the nanoscale dimension that can be used for the detection of various analytes
Nanosensor Nanosensor is a device for sensing chemicals or biological agents, in which a small portion of the device operates at the nanoscale.

DETAILED DESCRIPTION OF THE INVENTION

Accordingly the present invention provides a squaraine based fluorescent probe for thiol imaging, selective labeling of serum albumin protein, dye-protein complexes for the pH monitoring and a process for the preparation thereof. The process comprises of the squaraine dye having Formula 1 that detects and image thiol content inside live cells when the dye is prepared in 30% ACN/25 mM phosphate buffer with a pH of 8.0 and the dye forms self-assembled system when prepared in 25 mM phosphate buffer which has application in labeling of serum albumin proteins either covalently or non covalently at basic pH and acidic pH respectively giving "turn-on" green fluorescence corresponding to covalent labeling and "turn-on" NIR fluorescence corresponding to noncovalent labeling. The interaction being reversible with the pH of the solution and also shows high selectivity towards serum albumin proteins among thiol and nonthiol containing proteins and thiol containing small organic molecules. The dye protein complexes prepared in different ratios detects pH variations with high sensitivity in different regions of the pH scale ranging from 4.6 to 11.6 and with 1:6 ratio of dye protein composite detects pH variations inside live cells.

In the present invention, formula 1 prepared in 30% ACN/25 mM phosphate buffer with a pH of 8.0 detects and image thiol content inside live cells.

In the present invention, formula 1 label serum albumin protein among other biologically relevant materials, selectively, through non covalent binding at pH 4.2.

Squaraine dye of formula 1 can label serum albumin protein among other biologically relevant materials, selectively, through covalent binding at pH 8.2.

In the present invention the formula 1 gives "turn-on" green fluorescence for covalent mode of labeling.

In the present invention the formula 1 gives "turn-on" NIR emission for non covalent mode of labeling.

In present invention of the dye-protein complexes of various ratios detects with high level of sensitivity the pH variations in different regions of the pH scale.

In present invention the 1:6 Sq-BSA as well as Sq-HSA complex can detect pH variations in biological cell samples.

In the present invention the labeling process in the detection of pH variation is reversible. In the present invention, a novel unsymmetrical squaraine dye of formula 1 has been synthesized. Squaraine dye of Formula 1 is prepared in different solvent conditions and can be used for various applications. Formula 1 when prepared in 30% ACN/phosphate buffer exists in their monomeric state, while the molecule taken in phosphate buffer starts to form aggregates. Formula 1 prepared in 30% ACN/phosphate buffer at a pH 8.0 (maximum reactivity was observed at this pH condition) can be used for the detection of thiols selectively among other biologically relevant materials. The high sensitivity (2 nM) of the dye towards thiols helps for the detection of minor thiol fluctuations (milli molar to micro molar range) inside live cells.

Accordingly, the present invention provides a squaraine dye of Formula 1 which detects and image thiol content inside live cells when the dye is prepared in 30% ACN/25 mM phosphate buffer with a pH of 8.0. The dye in the self-assembled state label serum albumin proteins either covalently or noncovalently at specific pH of the solution.

Formula 1

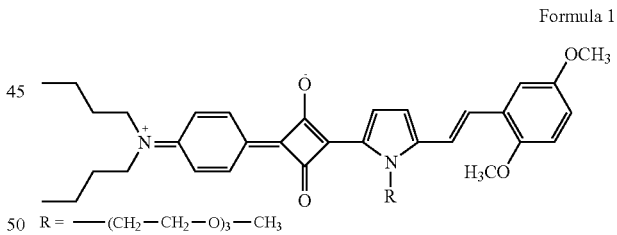

$R = \text{---}(CH_2\text{---}CH_2\text{---}O)_3\text{---}CH_3$

The probe 1 specifically binds with the serum albumin proteins noncovalently at lower pH and gives a "turn-on" NIR emission whereas it binds covalently at higher pH giving "turn-on" green fluorescence. Since the probe detects serum albumin proteins selectively in presence of other thiol containing small molecules, the probe can be used as an excellent sensor for serum albumin proteins. The dye-protein complexes of various ratios can be used to detect the pH variations in a broad window from 4.6-11.6 with high sensitivity. Due to the high biocompatibility and water solubility, the dye protein complex is useful for ratiometric detection of minor pH variations inside cellular environment. The dye prepared in phosphate buffer helps to label serum albumin protein selectively among other thiol and non-thiol containing proteins and thiol containing small molecules. The interaction of the dye with protein at a pH 4.2 is purely noncovalent with "turn-on" NIR emission. While that at a pH 8.2 is purely covalent with "turn-on" green emission. Since the molecule at two different pH conditions give signals at two different spectral regions, the accuracy of the measurement can be compared.

Formula 1 prepared in phosphate buffer complexed with proteins in different ratios helps to detect pH variations from 4.6-11.6 with high sensitivity. The 1:6 Sq-BSA complex can be used as an efficient ratiometric fluorescent probe for the sensitive detection of pH variations inside living cells.

A flowchart for using the unsymmetrical Squaraine dye of formula 1 for the detection of thiol, labeling of serum albumin protein and pH monitoring is shown in FIG. 16.

In order to facilitate a better understanding of the invention a detailed description of the preferred embodiments of the present invention will now be explained with reference to the accompanying drawings. It needs to be understood that the disclosed embodiments are merely exemplary of the invention, which may be embodied in various forms. Therefore, the details disclosed herein are not to be interpreted as limiting but merely as the basis for the claims, and as a basis for teaching one skilled in the art how to make or use the invention.

Compound 1 ((E)-2-(4-(dibutylamino)phenyl)-4-(5-(2,5-dimethoxystyryl)-1-(2-(2-(2-methoxyethoxy)ethoxy)ethyl)-1H-pyrrol-2-yl)-3-hydroxycyclobut-2-enone) is synthesized using compound 2 (styrylpyrrole chromophore) and compound 3 (semi squaraine of N,N dibutyl aniline) following scheme 1. 0.3 mmol of 2 and 0.3 mmol of 3 were dissolved in 30 mL of isopropanol and stirred well. 1 mL of TBOF was added. After refluxing for 12 h, the reaction mixture obtained was cooled followed by the removal of isopropanol by distillation. The crude product is precipitated from petroleum ether followed by filtration. It is then redissolved in $CHCl_3$ and further purified by column chromatography over silica gel using 2% $MeOH/CHCl_3$ using Scheme 1. The product is then characterized by UV, $^1H$ NMR, $^{13}C$ NMR and HRMS.

Formula 1 dissolved in 30% ACN/25 mM phosphate buffer at pH 8.0 mixture detects thiols with the quenching of absorbance at 670 nm with concomitant formation of new band at 380 nm (FIG. 1a) and excitation at 380 nm resulted in a "turn-on" fluorescence at 510 nm with simultaneous quenching of 700 nm emission (FIG. 1b). Similarly excitation at 640 nm resulted in a quenching of fluorescence at 700 nm (FIG. 1c).

Formula 1 prepared in 30% ACN/25 mM phosphate buffer at pH 8.0 shows high selectivity towards thiol containing molecules which was clear from the plot of fluorescence intensity at 510 nm ($\lambda_{exc}$ @ 380 nm) against different amino acids (FIG. 2). Thiol containing molecules like GSH, Cys and Hcy shows fluorescence enhancement at 510 nm ($\lambda_{exc}$ @ 380 nm) while other amino acids do not show much fluorescence enhancement. Sq detects GSH quantitatively with high sensitivity (2 nM) (FIG. 3). Formula 1 prepared in 30% ACN/25 mM phosphate buffer is used for monitoring thiol variations inside cells. Sq dye prepared in 30% ACN/25 mM phosphate buffer is incubated to the cells which were already treated with NEM (which was used to vary the concentration of the thiol content inside the cells) of concentrations $3\times10^{-6}$ to $3\times10^{-3}$ M showed a gradual fluorescence change thereby confirming the probe ability to detect minor thiol fluctuations inside cells (FIG. 4a and Figure). The formula 1 dissolved in acetonitrile showed absorption maximum at 670 nm, where the molecule exists in monomeric state, while 1 in 25 mM phosphate buffer showed a broad absorption from 550-850 nm ranges due to aggregation of formula 1. The aggregation was confirmed by temperature-dependent UV/Vis and emission spectroscopic studies in 15% acetonitrile/water mixture (FIG. 5a and FIG. 5b). The self-assembly of Sq was established further by atomic force microscopy (AFM), transition electron microscopy (TEM) and DLS analysis. AFM and TEM analysis revealed the formation of spherical aggregates of the dye with diameters ranging from 100-300 nm (FIGS. 6a and 6b). The dynamic light scattering (DLS) measurements of a buffer solution containing Sq (6 μM) showed aggregates with a mean diameter of 200 nm (FIG. 6c). Formula 1 prepared in 25 mM phosphate buffer solution at a pH of 4.2 labels serum albumin proteins noncovalently, which is evident from the UV-vis and emission spectroscopic studies. The broad absorption (550-850 nm) corresponding to the absorption of Sq aggregates narrowed with a turn-on fluorescence at 700 nm exc @ 640 nm) emission upon addition of BSA protein was observed (FIGS. 7a & 7b). The solution of the Sq dye in phosphate buffer has a blue color but nonemissive (FIG. 7c, top). Upon addition of BSA, the color of the dye is changed to light green which upon excitation with a laser pointer showed a red emission (FIG. 7c, bottom). At higher pH, 8.2, formula 1 prepared in 25 mM phosphate buffer solution interacts covalently with serum albumin proteins. The broad absorption (550-850 nm) corresponding to the absorption of Sq aggregates quenched with concomitant formation of an absorption at 380 nm was observed (FIG. 8a). Similarly emission spectra showed a "turn-on" fluorescence response at 480 nm ($\lambda_{exc}$ @ 380 nm) (FIG. 8b). The corresponding absorption and emission color changes of the dye is shown in the photographs in FIG. 8 e. From the photographs it is clear that the light blue solution of Sq becomes pale yellow in color with a green emission upon the addition of the BSA protein in the phosphate buffer at a pH 8.2. Probe 1 in the 25 mM phosphate buffer showed high selectivity towards BSA and HSA protein in the presence of other competitive molecules having thiol as functional group. At a lower pH (4.2), only BSA and HSA showed a fluorescence enhancement at 700 nm ($\lambda_{exc}$ @ 640 nm) whereas no fluorescence enhancement in the NIR region was observed upon the addition of even 10 equivalence of other thiol and nonthiol containing proteins (FIG. 9a). At a higher pH (8.2), BSA as well as HSA showed an enhancement in the fluorescence intensity at 480 nm ($\lambda_{exc}$ @ 380 nm) indicating the covalent labeling whereas even 10 equivalence of thiol containing proteins such as heamoglobin, glutathione reductase, bromelain were unable to produce fluorescence enhancement at 480 nm (FIG. 9b). From the emission spectra (FIG. 10) it is clearly evident that the probe shows high selectivity towards serum albumin proteins in presence of small thiol containing molecules. The noncovalent and covalent interactions of the albumins HSA and BSA with the dye is found to be highly reversible for several cycles using a 1:6 Sq-BSA (or 1:6 Sq-HSA) complex at lower and higher pH values of 5.8 to 7.4 (FIG. 11). Sq-BSA complexes of different ratios ranging 1:12 to 1:1/12 were used to detect pH variations within the broad pH window of 4.6 to 11.6. The 1:12 Sq-BSA complex sense the region 4.6-6.4, 1:6 for 5.8-7.4, 1:1 for 7.2-8.8, 1:1/6 for 8.6-10.2 and 1:1/12 for 10.2-11.6 (FIG. 12 & FIG. 13). The 1:6 Sq-BSA complex whose pH sensitivity lies within the physiological region and due to the ratiometric fluorescence response (FIG. 14) this system was used for monitoring minor pH fluctuations inside cells ratiometrically. The dye labeled protein is imported into Hep-G2 cells grown in wells of different pH 6.5, 7.0 and 7.5. The fluorescence variation in the cells with pH fluctuations is shown in FIG. 15. Quantitative data for pH measurements in cells were obtained using bio-rad image data explorer software (table 2).

Novel Features of the invention are:—
1) The molecule can be used for the detection of milli molar to micro molar thiol fluctuations that produced during small oxidative stresses inside the cells.
2) The fluorescent probe in the present invention specifically switches the mode of interaction with proteins between a noncovalent and covalent labeling, which can be controlled with an external stimulus resulting in distinct signal response is a new and novel approach.
3) The molecule can detect serum albumin protein at two different pH conditions which give signals at two different spectral regions, which helps to check the accuracy of the measurement.
4) Relatively simple probe that can be used to detect pH variations in a broad region with high sensitivity is still not known. The dye protein-complex that was prepared just by mixing in different ratios can be used to detect pH from 4.6-11.6 with high sensitivity.

The following examples are given by the way of illustration and therefore should not construe to limit the scope of the invention.

Example 1

Preparation of Formula 1

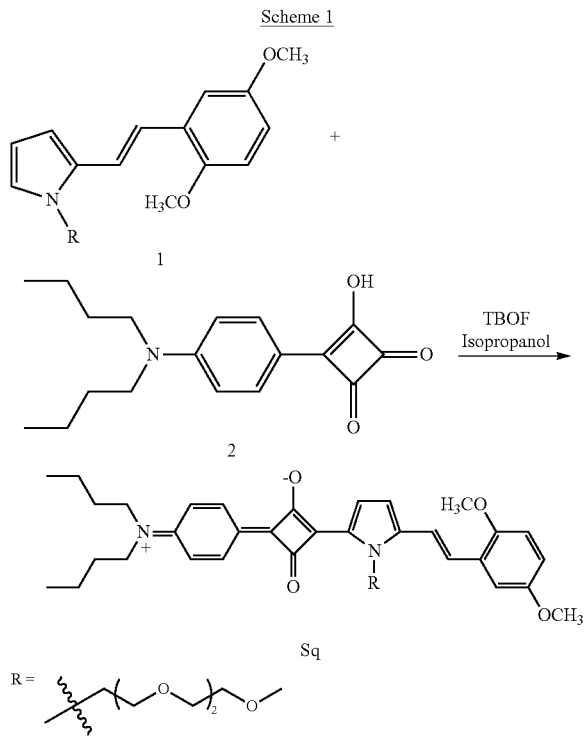

0.3 mmol of 2 and 0.3 mmol of 3 were dissolved in 30 mL of isopropanol and stirred well. 1 mL of TBOF was added. After refluxing at 80° C. for 12 h, the reaction mixture obtained was cooled followed by the removal of isopropanol by distillation. The crude product precipitated from petroleum ether was filtered and redissolved in CHCl₃ and further purified by column chromatography over silica gel using 2% MeOH/CHCl₃. Yield 40-45%. And the product was characterized by UV, $^1$H NMR, $^{13}$C NMR and HRMS.

$^1$H NMR (500 MHz, CDCl₃, δ): 8.3 (d, 2H, Ar H), 7.92 (d, 1H, Ar H), 7.64 (d, 1H, vinylic, J=16.5 Hz), 7.35 (d, 1H, vinylic, J=16.5 Hz), 7.16 (s, 1H, Ar H), 6.96 (d, 1H, Ar H), 6.86 (d, 2H, Ar H), 6.71 (d, 2H, Ar H), 4.98 (t, 2H, —NCH₂), 3.87 (s, 6H, —OCH₃) 3.83 (t, 2H, —OCH₂), 3.55 (t, 4H, —NCH) 3.36-3.55 (m, 8H, —OCH₂), 3.28 (s, 3H, —OCH₃), 1.63 (m, 4H, CH₂), 1.41 (m, 4H, CH₂), 0.98 (t, 6H, CH₃). $^{13}$C NMR (CDCl₃, 150 MHz) δ 13.88, 20.23, 29.59, 47.15, 51.10, 55.83, 56.15, 58.87, 70.49, 71.00, 71.01, 71.99, 112.15, 112.22, 114.25, 115.39, 116.86, 119.68, 125.55, 126.07, 129.77, 130.50, 132.39, 149.64, 152.07, 152.64, 153.75, 173.61, 178.80, 180.20, 181.41. FAB-MS: [M]⁺ Calcd for C₄₀H₅₃NO₇, 659.85. found 659.42.

Example-2

Procedure for Noncovalent Labeling of Serum Albumin Protein

Stock solution of Sq (1.2×10⁻³ M) was prepared in acetonitrile and stock solution of BSA protein (2.4×10⁻³M) was prepared in 25 mM phosphate buffer at pH 4.2. 15 µL of Sq from the stock solution is added to the 25 mM phosphate buffer at pH 4.2, to make the resulting concentration of the solution into 6×10⁻⁶ M. To this solution different volumes ranging from 7.5-150 µL of BSA protein were added and the absorption and emission spectra were recorded each time after 20 minutes. The broad absorption (550-850 nm) corresponding to the absorption of Sq aggregates narrowed with a turn-on fluorescence at 700 nm (λexc @ 640 nm) emission was observed.

Example-3

Procedure for Covalent Labeling Serum Albumin Protein

Stock solution of Sq (1.2×10⁻³ M) was prepared in acetonitrile and stock solution of BSA protein (1.2×10⁻³ M) was prepared in 25 mM phosphate buffer at a pH of 8.2. 15 µL of Sq from the stock solution is added to 25 mM phosphate buffer at pH 8.2, to make the resulting concentration of the solution to 6×10⁻⁶ M. To this solution different volumes ranging from 1.5-36 µL of BSA protein were added and the absorption and emission spectra were recorded at 15 minutes interval. The broad absorption (550-850 nm) corresponding to the absorption of Sq aggregates quenched with concomitant formation of an absorption at 380 nm was observed (FIG. 8a). Similarly emission spectra showed a "turn-on" fluorescence response at 480 nm ($\lambda_{exc}$ @ 380 nm) (FIG. 8b).

Example-4

Procedure for the Preparations of Various Dye-Protein Complexes for pH Monitoring Sq (1.2×10⁻³ M) stock solution was prepared in acetonitrile and BSA protein (2.4×10⁻³M) stock solution was prepared in 25 mM phosphate buffer. For the preparation of various Sq-BSA complex in different ratios (1:12, 1:6, 1:1, 1:1/6, 1:1/12) were taken into various pH solutions (4.2-

11.6) and their emission spectra were recorded after keeping the solution for 1 hour. Emission spectra showed a "turn-on" fluorescence response at 480 nm ($\lambda_{exc}$ @ 380 nm) while the fluorescence response at 700 nm ($\lambda_{exc}$@ 640 nm) got quenched.

Example-5

Cell Culture (Hep-G2 Cells)

The culture medium was prepared by dissolving 13.4 g of DMEM-high glucose (Sigma, USA) in 1 L of distilled water. Sodium bicarbonate (3.7 g $L^{-1}$) was added to the medium and the pH of the medium was adjusted to 7.4. This medium was then sterilized by passing through a sterile filter assembly fitted with a 0.22 μm filter (Millipore, USA) using a vacuum pump. Later, the medium was stored in pre-sterilized Borosil polypropylene bottles, at 4° C., until further use. To the prepared culture medium an antibiotic mixture (20 μL $mL^{-1}$ of 100× concentrate, Sigma, USA) was added. Fetal bovine serum (FBS) (Sigma, USA) was also added to the medium to give a final concentration of 10% (to 900 mL medium, 100 mL of FBS was added).

Hep G2 cells (Human Hepatocellular carcinoma cell lines), which was obtained, from National Centre for Cell Science, Pune, India, were stored in cryovials at −196° C. in liquid nitrogen, in a medium containing 70% FBS, 10% dimethyl sulfoxide (DMSO) and 20% DMEM. For revival, the vials were thawed by placing them in a water-bath maintained at 37° C. for 2-3 minutes followed by centrifugation at 3000 rpm for 3 minutes. Supernatent was removed and the pellet after suspending in medium were transferred into a radiation sterilized culturing flask, T-25 $cm^2$ (BD Biosciences) inside the laminar flow. Subsequently, the flask was placed in a $CO_2$ incubator for 2 h. The viable cells stick to the culture flask while the dead cells remain in the medium. Later the medium was replaced with fresh medium containing 10% FBS and incubated till a cell confluency of 70-80%. The medium was then discarded following desired confluency. Following confluency, since the Hep G2 cells are adherent in nature, they were trypsinised by using 1 mL of trypsin (0.25%)—EDTA (0.53 mM) buffer containing 0.9% sodium chloride for 5 mM. The cells were then transferred to a centrifuge tube and centrifuged at 2000 rpm for 3 min, followed by the removal of the supernatant.

For sub culturing, fresh DMEM containing 10% FBS was added under aseptic conditions. Cells were flushed with the help of pipette (1 mL) until the cells are completely dispersed into the medium. The cells were then diluted in a sterile complete medium at 1:3 times and transferred into fresh culture flasks. Then the flasks were placed inside $CO_2$ incubator.

Procedure for the Imaging of pH Changes in Cells:

The 1:6 Sq-BSA Complex whose sensitivity of pH lies within the physiological region and due to the ratiometric fluorescence response (FIG. 14) was used in this system for monitoring minor pH fluctuations inside cells ratiometrically. Hep-G2 cells were pre-incubated with phosphate buffer of different pH (6.5, 7.0, 7.5) and kept for 10 minutes. The 1:6 Sq-BSA complex ($1\times10^{-6}$ M), which was prepared by mixing 5 μl of Sq ($4\times10^{-5}$ M, prepared in acetonitrile) and 15 μl of BSA protein ($1.2\times10^{-3}$ M, prepared in phosphate buffer 4.2) was added to each cells and kept for 10 minutes. The cells were then centrifuged and diluted for 2 times and then images has taken using confocal fluorescence microscope using alexa (640 nm exc) and DAPI (380 nm exc) as filters. The fluorescence variation in the cells with pH fluctuations is shown in FIG. 15. With respect to the pH of the wells the fluorescence intensity from the DAPI image was enhanced and the alexa image got quenched. Quantitative data for pH measurements in cells were obtained using bio-rad image data, explorer software (table 2). The viability of the cells after incubation of Sq-BSA complex was confirmed by the bright-field transmission measurements (FIG. 15 c, bottom).

TABLE 2

| Fluorescence Intensity | pH 6.5 | pH 7.0 | pH 7.5 |
|---|---|---|---|
| DAPI Image | 8.5 | 24.61 | 30.18 |
| Alexa Image | 39.84 | 21.47 | 18.08 |

Example-6

Procedure for the Detection of Minor Thiol Fluctuations Inside HepG2 Cells

Hep-G2 cells were pre-incubated with NEM of various concentrations ($3\times10^{-3}$ M to $3\times10^{-6}$ M) and kept for 15 minutes. 50 μl of formula 1 ($1.2\times10^{-3}$M) which was prepared in acetonitrile is added to each cells and kept for 10 minutes. The cells were then centrifuged and diluted for 2 times and then images were-taken using confocal fluorescence microscope using alexa (640 nm exc) and DAPI (380 nm exc) as filters. The cells which were pretreated with NEM of higher concentration showed a weak green fluorescence upon introduction of Sq dye, while the cells which are pretreated with NEM of lower concentration gave an enhanced fluorescence intensity (FIG. 4a). From the fluorescence intensity plot (FIG. 4b) it was clear that the fluorescence intensity showed a gradual quenching with respect to increase in concentration of NEM, thereby confirming the probe ability to detect minor thiol fluctuations inside cells.

Example-7

Absorption and Emission Spectral Changes of Formula 1 with the Addition of Glutathione Formula 1 dissolved in 30% ACN/25 mM phosphate buffer mixture gave absorption at 670 nm and emission at 700 nm. Addition of glutathione (GSH) at pH 8.0 resulted in the quenching of absorbance at 670 nm with concomitant formation of new band at 380 nm (FIG. 1a). Emission spectra also showed a similar behavior upon addition of GSH. When excited at 380 nm, the emission spectrum of Sq-GSH adduct exhibited a new band at 510 nm with a green fluorescence, where as the fluorescence intensity at 700 nm corresponding to the emission of Sq dye was quenched (FIG. 1b-1c). These changes in the absorption and emission spectra are attributed to the addition of thiol group to cyclobutene ring, which resulted in the formation of new strongly fluorescent chromophore.

Example-8

Selectivity and Sensitivity Studies of Formula 1 Toward Thiols

In order to investigate the selectivity, formula 1 was treated with 20 equivalence of 9 different amino acids (FIG.

2) as well as 1 equivalence of thiol containing biomolecules like Cys, Hcy and GSH. The nonthiolated molecules did not induced any significant fluorescence changes in Sq, and only Cys, Hcy along with GSH elicited a dramatic increase in the fluorescence intensity. Moreover, in the presence of these competitive species, the GSH (the most important biologically relevant thiol containing molecule) still resulted in similar fluorescence changes, suggesting that the probe is highly selective to GSH among the 9 different amino acids there by the interference from other amino acids present inside the cells can be avoided. The fluorescent intensity at 510 nm ($\lambda_{exc}$ @ 380) with GSH concentration shows a linear relationship with a detection limit of 2 nM, which indicates that Sq could detect GSH quantitatively with high sensitivity (FIG. 3).

Example-9

Temperature Dependent Absorption and Emission Spectral Changes of Formula 1

The formula 1 dissolved in acetonitrile showed absorption maximum at 670 nm, where the molecule exists in monomeric state, while 1 in 25 mM phosphate buffer shows a broad absorption from 550 to 850 nm ranges due to aggregation of formula 1. The aggregation was confirmed by temperature-dependent UV/Vis and emission spectroscopic studies in 15% acetonitrile/water mixture. When the solution temperature was increased from 25°-70° C., a significant increase in the intensity at 680 nm absorption was observed, indicating the disassembly of the aggregated dyes at elevated temperature (FIG. 5a). Similarly, the gradual increase in the emission intensity observed with the increase in the solution temperature suggests a gradual conversion of the non-fluorescent Sq aggregates into the fluorescent dye monomer (FIG. 5b).

Example-10

Characterization by Morphological Studies

The self-assembly of Sq was established by atomic force microscopy (AFM), transition electron microscopy (TEM) and DLS analysis. AFM and TEM analysis revealed the formation of spherical aggregates of the dye with diameters ranging from 100-300 nm (FIGS. 6a and 6b). The dynamic light scattering (DLS) measurements of a buffer solution containing. Sq (6 µM) showed aggregates with a mean diameter of 200 nm (FIG. 6c).

Example-11

Noncovalent Labeling of Serum Albumin Protein Using Formula at pH 4.2

Even though noncovalent interaction of serum albumin proteins and covalent interaction of thiol containing small molecules with squaraine dyes are known in individual cases, achieving both type of interaction by a single probe in a reversible fashion with an external stimulus remains challenging. Therefore, the first and foremost task was identifying an appropriate switchable dye molecule, which is stable at a broad pH window with distinct emission wavelengths during the different modes of interactions and having a tunable pH responsive interaction. Sq was found to be stable at a broad range of pH (2-12). Sq (6 µM) in 25 mM phosphate buffer at a lower pH of 4.2, showed a broad absorption band between 550-850 nm (FIG. 7a). Addition of BSA protein to this solution resulted in the formation of a narrow absorption band at 670 nm. This absorption band is similar to the absorption of Sq in acetonitrile in which the molecule exists in the monomeric state. This observation indicates that the addition of BSA protein induces disassembly of the Sq aggregates, which is further confirmed by change in the fluorescence property. Sq (6 µM) in a 25 mM phosphate buffer (pH 4.2) has no emission at 700 nm due to the aggregation. Upon addition of BSA protein, a gradual enhancement in the fluorescence intensity at 700 nm was observed (FIG. 7b). This fluorescence enhancement is due to the disassembly of aggregates and the consequent noncovalent interaction between Sq and BSA protein. The solution of the Sq dye in 25 mM phosphate buffer has a blue color and at this stage the dye is non emissive (FIG. 7c, top). Upon addition of BSA, the color of the dye is changed to light green which upon excitation with a laser pointer showed a red emission (FIG. 7c, bottom).

Example-12

Covalent Labeling of Serum Albumin Protein Using Formula 1 at pH 8.2

At higher pH of 8.2, addition of BSA to Sq (6 µM) in 25 mM phosphate buffer resulted in quenching of the characteristic broad absorption band corresponding to Sq aggregates with the formation of a new band at 380 nm. Simultaneously the absorption of tryptophan chromophore in the BSA protein at 279 nm is increased (FIG. 8a). The dye initially has no emission in the 480 nm region on 380 nm excitation. However the addition of protein resulted in the formation of a band at 480 nm (FIG. 8b). The corresponding absorption and emission color changes of the dye is shown in the photographs in FIG. 8c. From the photographs it is clear that the light blue solution of Sq becomes pale yellow in color with a green emission upon the addition of the BSA protein in the 25 mM phosphate buffer at a pH of 8.2. These changes in the absorption and emission spectra are attributed to the addition of the thiol group of the cysteine residue present in the BSA, to the cyclobutene ring of the Sq, which results in the breaking of the dye conjugation length. As a result new strongly emitting green fluorescent chromophore is generated, which signals the labeling process.

Example-13

Selective Detection of Serum Albumin Protein Among Other Thiol and Nonthiol Containing Proteins The labeling by the self-assembled probe 1 in the 25 mM phosphate buffer showed high selectivity towards BSA and HSA protein in presence of other competitive molecules having thiol functional group. At a lower pH (4.2), both BSA and HSA got labeled as indicated by the fluorescence enhancement at 700 nm whereas no fluorescence enhancement in the NIR region was observed upon the addition of even 10 equivalence of other thiols and nonthiol containing proteins (FIG. 9a). This selectivity apparently originates from the Sq disassembly driven by the molecular recognition sites of the serum albumin proteins. At a higher pH of 8.2, BSA as well as HSA showed green emission at 480 nm indicating the covalent labeling whereas even 0.10 equivalence of thiol containing proteins such as heamoglobin, glutathione reductase, bromelain were unable to produce fluorescence enhancement at 480 nm (FIG. 9b). This result shows that Sq dye in the 25 mM phosphate buffer at higher pH also exists in the self-assembled state and hence could not undergo any chemical reaction with other thiol containing proteins.

Example-14

Selective Detection of Serum Albumin Protein Among Other Thiol Containing Small Molecules The selectivity of our nanoprobe towards serum albumin proteins from small thiol containing molecules like cysteine, homocysteine, glutathione, mercaptoethanol, dithiothreitol, cystamine and thioglycolic acid at a higher pH of 8.2, where the dye is expected to undergo thiol alkylation reaction is investigated. We found that addition of 10 equivalent of thiol containing small molecules was unable to generate much fluorescent enhancement in the 480 nm region. Bar diagram represents the selectivity of Sq ($6 \times 10^{-6}$ M) for BSA and HSA protein ($6 \times 10^{-6}$ M) from other small thiol containing molecules (FIG. 10) which clearly indicate that the probe in its self-assembled state is able to detect serum albumin protein among other thiol containing small molecules.

Example-15

Reversibility of the Noncovalent and Covalent Interactions of the Albumins with the Dye The noncovalent and covalent interactions of the albumins HSA and BSA with the dye is found to be highly reversible for several cycles using a 1:6 Sq-BSA complex at lower and higher pH values of 5.8 to 7.4 (FIG. 11). At a pH of 7.4, where the molecule is covalently attached with the protein, the addition of an acid resulted in an enhancement of the 700 nm emission with the concomitant quenching of 480 nm emission. This indicates that the covalently attached Sq dye is detached from the protein and rebound with in the protein cavities. Subsequent addition of a base reversed the process by enhancing the 480 nm emission with the simultaneous quenching of the 700 nm emission. This switching was observed at least for four cycles of the acid-base additions.

Example-16 pH Monitoring Studies

Sq-BSA complexes of different ratios ranging 1:12 to 1:1/12 were used to detect pH variations anywhere within a broad pH window of 4.6 to 11.6. This is the first report in which a same probe is used to detect pH variations in a broad region with high sensitivity. The 1:12 Sq-BSA complex sense the region 4.6-6.4, 1:6 for 5.8-7.4, 1:1 for 7.2-8.8, 1:1/6 for 8.6-10.2 and 1:1/12 for 10.2-11.6 (FIG. 12). The variation in the sensitivity is due to the change in kinetics which depends upon on the number of Sq dye molecules that effectively reacts with proteins and the effect of base catalysis. When BSA concentration is more as in the case of 1:12 and 1:6 ratios Sq molecules exists in their monomeric state and can undergo nucleophilic addition reaction even in the acidic pH also. At higher concentration of proteins Sq dyes exists as monomers undergo nucleophilic addition reaction upon increasing pH and hence the emission of the dye at 700 nm decreases. Thus for 1:12 and 1:6 Sq-BSA the change in fluorescence intensity at 480 nm and 700 nm regions are highly ratiometric (FIGS. 12 & 13). At lower equivalence of proteins most of the Sq dyes are in their self-assembled state and undergo reaction with proteins only at a higher pH. Molecules in their aggregated state have to come to their monomeric state for the reaction to occur. As a result the fluorescence intensity variation at 700 nm has a little change with respect to increase in pH of the solution. Therefore for 1:1/6 and 1:1/12 fluorescence response is not ratiometric (FIGS. 12 & 13).

ADVANTAGES OF THE PRESENT INVENTION

1) The probe in its monomeric state detects thiols with high selectivity and sensitivity.
2) The probe prepared in 30% ACN/25 mM phosphate buffer can be useful for the detection of minor fluctuation in the thiol concentration inside live cells.
3) The same probe was used for both covalent and noncovalent labeling of serum albumin proteins by varying the pH of the solution.
4) The self-assembling nature of the squaraine dye provides high selectivity for covalent and noncovalent labeling of serum albumin proteins from other biorelevent molecules of amino acids and proteins.
5) Covalent and noncovalent labeling causes the "turn-on" fluorescence while interacting with Sq which helps in visualizing the process of labeling reaction immediately at the point of labeling in the presence of unreacted probes.
6) Labeling was found to be highly reversible and follows a fast kinetics.
7) The pH controlled covalent vs noncovalent labeling of Sq towards serum albumin protein is successfully utilized for monitoring minor pH variations in a wide region of pH from 4.6 to 11.6 by varying the ratio between the dye and protein.
8) The 1:6 Sq-BSA complex can be used as an efficient ratiometric fluorescent probe for the sensitive detection of pH variations inside living cells.

The invention claimed is:
1. A novel unsymmetrical Squaraine dye of Formula 1 and its complex thereof,

Formula 1

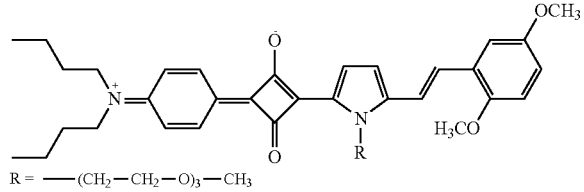

R = ——(CH$_2$—CH$_2$—O)$_3$—CH$_3$ wherein the complex is a complex of the unsymmetrical Squaraine dye of Formula 1 with a protein.
2. A nanoprobe comprising a combination of the Squaraine dye of Formula 1 of claim 1 with a protein in a dye to protein molar ratio of 1:12, 1:6, 1:1, 1:1/6 or 1:1/12, wherein the protein is bovine serum albumin or human serum albumin.
3. A nanoprobe comprising a combination of the Squaraine dye of Formula 1 of claim 1 with a protein in a dye to protein molar ratio of 1:6, wherein the protein is bovine serum albumin or human serum albumin.

4. The unsymmetrical Squaraine dye of Formula 1 of claim 1.

5. The complex of the unsymmetrical Squaraine dye of claim 1.

6. The complex of the unsymmetrical Squaraine dye of Formula 1 of claim 1, wherein the protein is bovine serum albumin or human serum albumin.

7. The nanoprobe of claim 2, wherein the protein is bovine serum albumin.

8. The nanoprobe of claim 2, wherein the protein is human serum albumin.

9. The nanoprobe of claim 3, wherein the protein is bovine serum albumin.

10. The nanoprobe of claim 3, wherein the protein is human serum albumin.

11. The complex of claim 1, wherein the complex is a complex of the unsymmetrical Squaraine dye of Formula 1 with a serum albumin protein.

12. The complex of claim 11, wherein the serum albumin protein is bovine serum albumin.

13. The complex of claim 11, wherein the serum albumin protein is human serum albumin.

\* \* \* \* \*